(12) United States Patent
Lee

(10) Patent No.: US 6,772,759 B2
(45) Date of Patent: Aug. 10, 2004

(54) HEALTH MASK WITH CHANNELIZED BREATH PASSAGEWAYS

(76) Inventor: Bookyung Lee, 136-302 Gwanak APT, 1102, Bisan-Dong, Dongan-Gu, Ahnyang-City, Kyunggi-Do (KR)

( * ) Notice: Subject to any disclaimer, the term of this patent is extended or adjusted under 35 U.S.C. 154(b) by 0 days.

(21) Appl. No.: 10/407,179

(22) Filed: Apr. 7, 2003

(65) Prior Publication Data

US 2003/0221690 A1 Dec. 4, 2003

(30) Foreign Application Priority Data

May 28, 2002 (KR) .............................. 20-2002-0016221 U

(51) Int. Cl.[7] .................................................. A62B 18/02
(52) U.S. Cl. .............................. 128/206.19; 128/201.15
(58) Field of Search ........................ 128/201.15, 201.17, 128/201.18, 201.23, 201.24, 201.25, 206.12, 206.13, 206.16, 206.17, 206.19, 206.21, 206.23, 206.24, 206.11, 206.22, 206.28, 207.13, 205.25; 2/9, 173, 206

(56) References Cited

U.S. PATENT DOCUMENTS

| | | | | |
|---|---|---|---|---|
| 2,810,386 A | * | 10/1957 | Reed ..................... | 128/201.15 |
| 2,888,920 A | * | 6/1959 | Mollering et al. ..... | 128/201.15 |
| 2,891,540 A | * | 6/1959 | Tietze ................... | 128/201.15 |
| 3,834,384 A | * | 9/1974 | Raines .................. | 128/201.15 |
| 3,888,246 A | * | 6/1975 | Lauer .................... | 128/201.17 |
| 4,452,240 A | * | 6/1984 | Moretti ................. | 128/201.18 |
| 5,727,544 A | * | 3/1998 | Miura ................... | 128/201.13 |
| 5,836,303 A | * | 11/1998 | Hurst et al. ........... | 128/206.24 |
| 6,173,712 B1 | | 1/2001 | Brunson | |
| 6,520,181 B2 | * | 2/2003 | Baumann et al. ...... | 128/206.19 |
| 6,609,516 B2 | * | 8/2003 | Hollander et al. ..... | 128/201.17 |
| 2002/0026943 A1 | | 3/2002 | Castiglione | |
| 2002/0056450 A1 | * | 5/2002 | Lee ........................ | 128/201.15 |
| 2003/0029454 A1 | * | 2/2003 | Gelinas et al. ......... | 128/205.27 |

FOREIGN PATENT DOCUMENTS

| | | |
|---|---|---|
| EP | 0469498 A2 | 7/1991 |
| WO | WO 00/74509 A1 | 12/2000 |

* cited by examiner

Primary Examiner—Teena Mitchell
(74) Attorney, Agent, or Firm—Nixon & Vanderhye P.C.

(57) ABSTRACT

Air-blocking material forms a concentrated passage in a health mask body that covers a user's nose and mouth where air is concentrated and passed through at inhalation and exhalation. Such concentrated passage maintains humidity and preserves heat due to the humid and warm respiration air produced at the time of exhalation. Moreover, frosting of eyeglasses is prevented by ensuring that the hot exhalation air does not flow upwardly when the patient wears eyeglasses.

8 Claims, 3 Drawing Sheets

HEALTH MASK WITH CHANNELIZED BREATH PASSAGEWAYS

BACKGROUND OF THE INVENTION

1. Field of the Invention

The present invention relates to a health mask, and more particularly to, a health mask that contains air-blocking material that blocks and directs breathing air along a defined passage. As cold air is inhaled in, a supporting cloth preserves respiration heat and humidity, produced at a prior time of breathing outwardly. This reduces the influx of cold air to the nose and maximizes inhalation of humid air into the nose. This also minimizes inhalation of dry and cold air from the outside, which exerts negative influence on cold symptoms. The present invention also pertains to an improved health mask that helps reduce production of frost on a user's eyeglasses at the time of exhalation.

2. Description of the Prior Art

Generally, a health mask is used by a patient who is afflicted with illness related to a respiratory organ such as coughing or a cold and who wishes to avoid direct contact with cold and dry outside air at the time of inhalation.

As illustrated by FIG. 1, this mask (10) typically includes a rectangular body (11), made of cloth material and of a size that can simultaneously cover a user's nose and mouth. An attachment or hanging string (13), attached on both left and right sides of body (11) can be hung upon a user's ears. FIG. 1 also reveals a typical needlework line that ensures the overlapping of an outer and inner cloth.

On the other hand, a patient with a cold may mitigate cold symptoms best when humid air is continuously inhaled instead of cold and dry outside air. When a patient with a cold applies and uses the prior general mask (10), the function of a mask is not optimized since inhalation of cold and dry air from the outside by the user can occur through an influx passage which forms between the left and right side of the user's face and the nose ridge that faces and comes into contact with the inner surface of body (11) at the time of inhalation.

In case of a user who wears eyeglasses, the user may further be inconvenienced with an unclear view due to the creation of frost on the surface of the eyeglasses due to hot moist breathing air also being discharged into the influx passage (i.e., the empty space situated between the nose ridge and left and right side of the face) at the time of exhalation.

It is desired for body (11) to retain relative humidity from the exhalation air being discharged to the outside so that dry air from the outside may be humidified as it is inhaled by the user as it passes through the cloth material of body (11). However there is a limit to the amount of humidity body (11) can maintain at a consistent level since respiration heat such as exhalation air (i.e., air from the nose and/or mouth of the user) is distributed to the entire body (11) and then discharged to the outside.

SUMMARY OF THE INVENTION

The present invention pertians to an improved health mask. The exemplary health mask includes a body (2) large enough to cover both the nose and mouth of a user. It is made of cloth material and includes an attachment hanging string (3) for the ears attached at the right and left side of body (2). A supporting cloth (4) is attached onto the inner surface of body (2) that corresponds to the nose and mouth, and air-blocking material (5) is fixed in the symmetrical arrangement of a pair of left and right inverted L-structures located between inner and outer cloths (4a) (4b) of the supporting cloth (4). This forms a more concentrated passage that fills up the otherwise empty space found between the left and right side of the nose where exhalation air is concentrated at the inner surface of body (2). Air-blocking material (5) blocks and curtails the influx of cold air into the respiratory organs. The supporting cloth (4) helps preserve respiration heat and humidity that are discharged from the user at the time of breathing. This helps maximize inhalation of humid air into the user's respiratory organs during inhalation while also minimizing inhalation of untreated dry air from the outside which would aggravate cold symptoms. This also helps reduce creation of frost on the user's eyeglasses at the time of exhalation.

BRIEF DESCRIPTION OF THE DRAWINGS

The aforementioned aspects and other features of the present invention will be explained in the following description, taken in conjunction with the accompanying drawings, wherein.

DETAILED DESCRIPTION OF THE INVENTION

The present invention will be described in detail by way of a preferred embodiment with reference to accompanying drawings.

Thus, the present invention is recommended as a measure to address the aforementioned problems. The purpose of the present invention is to offer a health mask that helps maintain the level of humidity in the mask body by concentrating the breath passage so as to enable a user to inhale humid air by humidifying cold and dry air from outside as it passes through the body of the mask at the time of inhalation.

The exemplary embodiment is comprised of cloth material and has a body with appropriate size to cover the nose and mouth. A string is installed on the left and right side of the body and hangs the mask from both ears of the user. A supporting cloth is attached onto the inner surface of the body that is directly proximate the user's nose and mouth in use.

The exemplary embodiment fills up an empty space otherwise formed between the inner surface of the body and both the left and right side of the nose. This provides a more concentrated breath passageway with concentration of breath steam by a symmetrical arrangement of a pair of left and right air-blocking structures located between the inner and outer supporting cloths. The present exemplary health mask is thus characterized by the inclusion of air-blocking material fixed in location so as to more optimally channelize a user's inhalation and exhalation air.

Figure 1:
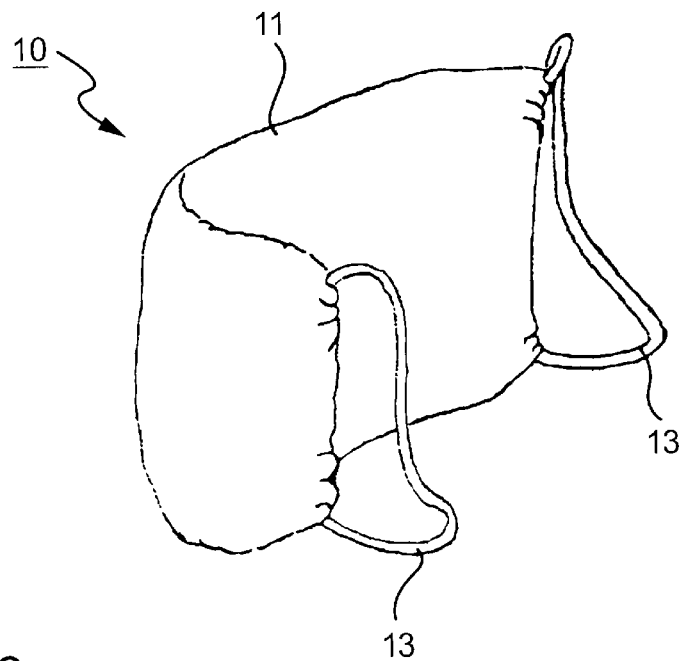
FIG. 1: illustrates a typical prior art health mask.
Figure 2:
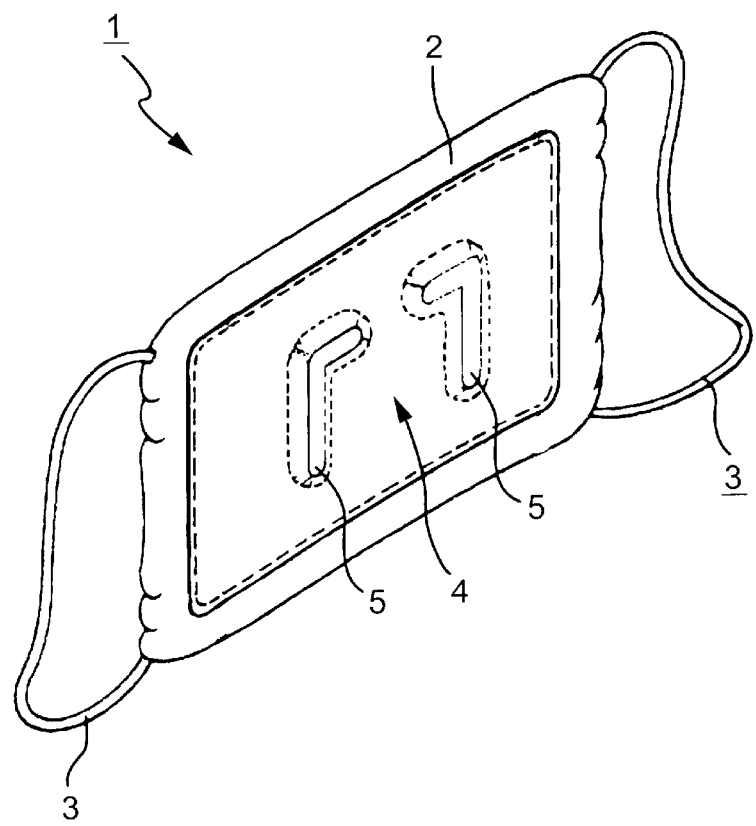
FIG. 2: illustrates outside features of a health maskaccording to an exemplary embodiment of the present invention.
Figure 3:
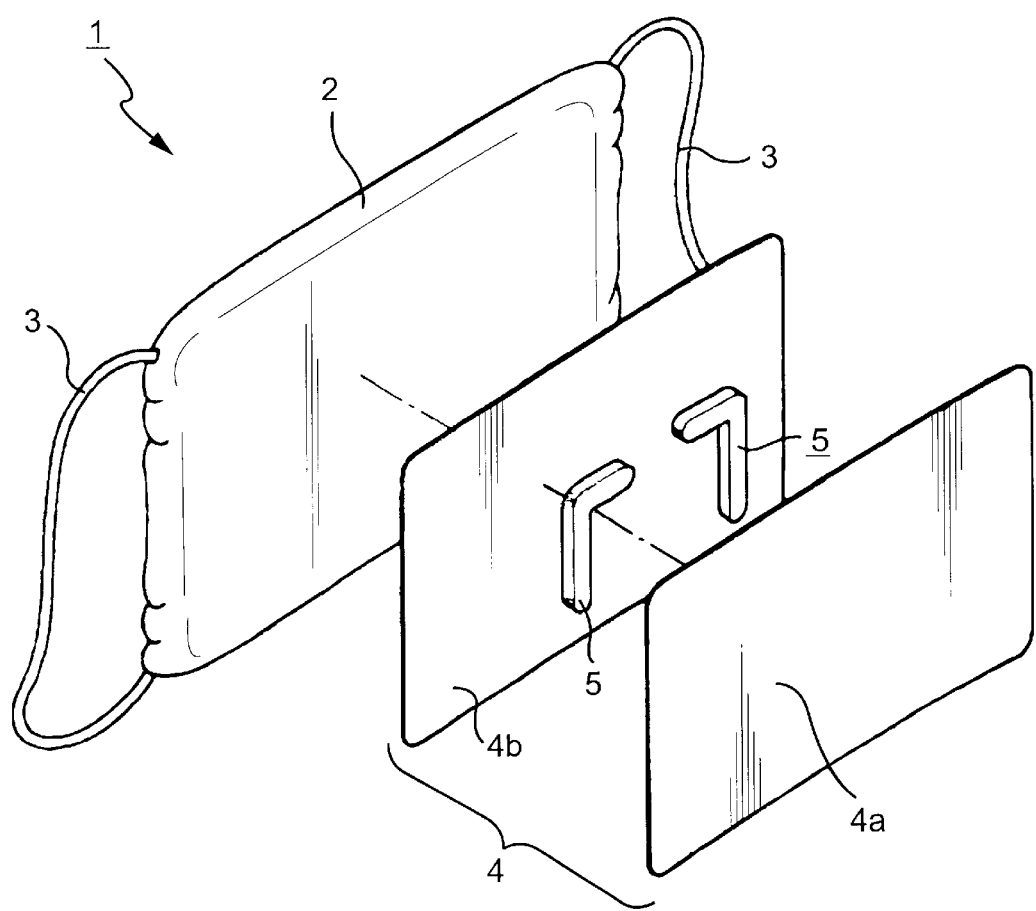
FIG. 3: further illustrates features of the exemplary health mask, shown in FIG. 2.
Figure 4:
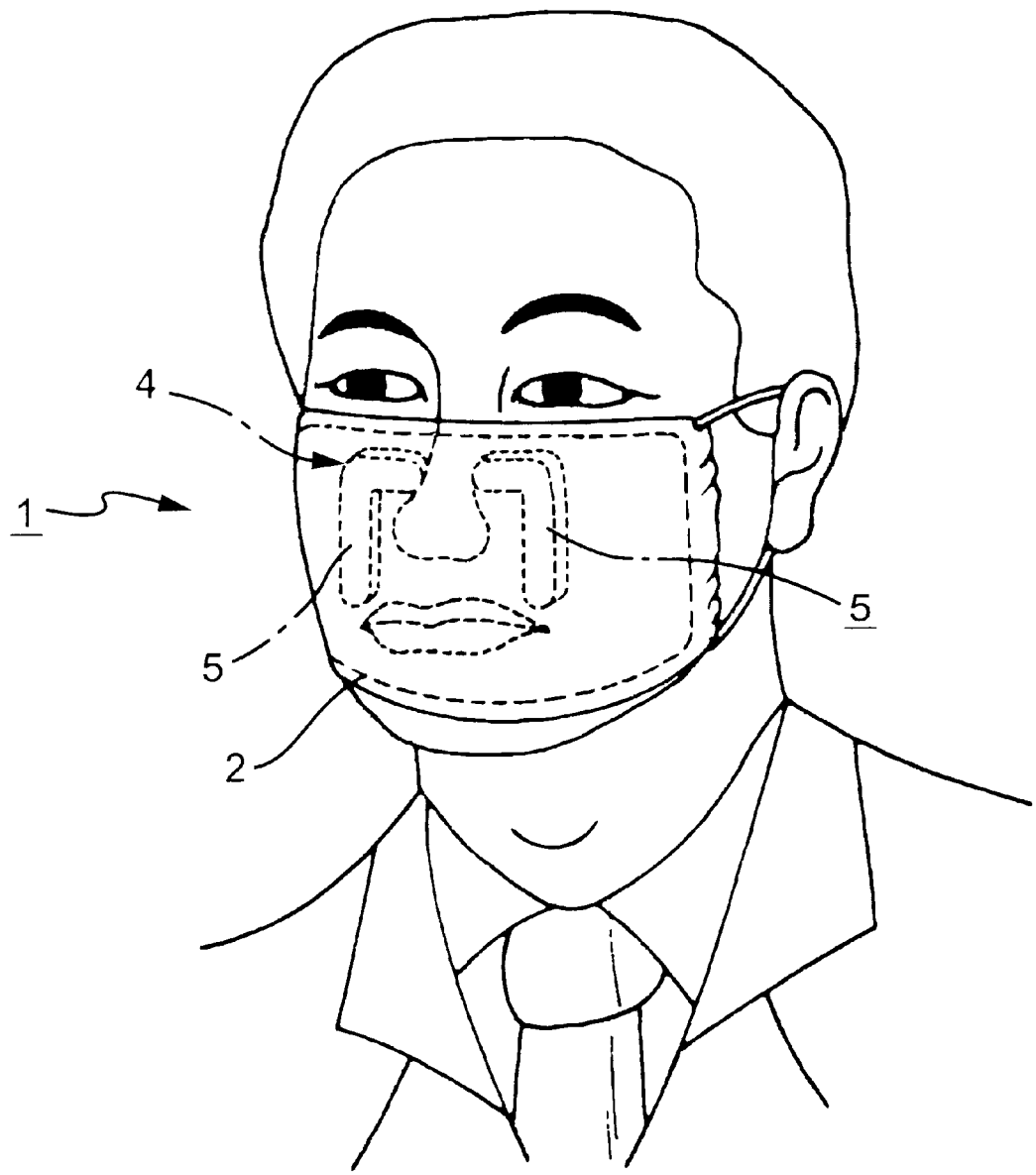
FIG. 4: illustrates usage of the exemplary health mask shown in FIG. 2.

FIG. 2 depicts the external features of the exemplary health mask and FIG. 3 depicts a decomposition of the exemplary health mask structures. FIG. 4 depicts a typical use of the exemplary health mark.

As shown in FIG. 2 or 4, the exemplary mask (1) is a sanitary consumable that covers part of the face to minimize direct contact of the user (e.g., a patient with a cold) from cold and dry exterior air. Mask (1) includes body (2), hanging strings (3), supporting cloth (4) and air-blocking material (5).

Body (2) includes rectangular cloth material of a size sufficient to cover a user's nose and mouth where the user's respiration heat such as breath and nose steam is discharged to the outside and where outside air is inhaled from the outside. On the left and right sides of body (2), a hanging string (3) is attached to enable the user to easily hang the string on both ears when applying the mask.

Supporting cloth (4) is attached on to the inner surface of body (2) that covers the nose and mouth and it includes overlapping inner and outer cloths (4a) (4b) sewn into place. Supporting cloth (4) is preferably either made of the same cloth material as body (2) or of other cloth material with an outstanding ability to preserve humidity and temperature while facilitating the passage of exhalation air from the nose and/or mouth into the interior and exterior.

Supporting cloth (4) retains air-blocking material (5) of symmetrical inverted L-shapes and situated for blocking air passage. The air-blocking structures are centered about the user's nose so as to substantially fill up the otherwise empty space that forms between the inner surface of body (2) and both the left and right sides of the user's nose. The blocking structures 5 are installed in a fixed manner between the inner and outer cloths (4a) (4b) of supporting cloth (4) where the breath steam is concentrated so that a concentrated passageway for breath steam is formed. It is preferred that the air-blocking structures (5) be sewn onto supporting cloth (4) so that they do not move from their desired positions between inner and outer cloths (4a) (4b).

The upper part of each air-blocking structure (5) preferably curves horizontally so that it comes into contact with the left and right side of the nose. The lower part preferably continues downwardly to form a generally inverted L-shaped device for blocking air that otherwise expands vertically so that it will terminate near the left and right sides of the user's lip. Use of flexible, elastic, light and soft material such as sponge material is preferred for use as the air-blocking material (5).

Supporting cloth (4) preferably supports the air-blocking material (5) using Velcro tape or another type of adhesive applicable to body (2) on the left and right sides of the frontal part so that the air blocks 5 can be attached easily into the inner surface of body (2) (e.g., by impact).

It is preferred that the concentrated air breath passage, formed on the inner surface of body (2) be situated at the inner surface of the body that corresponds to the space between the user's nose and mouth, so that the path where breath passes at the time of exhalation and the part where the air is inhaled from the exterior at the time of inhalation coincide.

When a patient with a cold applies and uses the exemplary mask (1), supporting cloth (4), comprised of inner and outer cloth (4a) (4b), is installed at the part that corresponds with the nose and mouth of the patient onto the inner surface of the body (2) that comprises mask (1). Between the inner and outer cloth (4a) (4b), the empty space that otherwise forms between the inner surface of body (2) and the left and right side of the nose is filled with air-blocking material (5) by a left and right symmetrical pair of structures installed to form concentrated passageways where exhalation air is concentrated.

Given the above mentioned condition, respiration heat such as exhalation air steam that streams out of the mouth and nose at the time of exhalation by the user does not leak out to the upper part or to the sides due to air-blocking material (5). Instead, the exhalation breath air is discharged to the exterior through the body's concentrated passage that pertains to the area between the aforementioned nose and mouth. Because of such exhalation passage, cloth material that pertains to the concentrated passage of body (2) assumes a higher temperature compared to the atmospheric temperature due to humidity and warm air included in the exhalation air that is discharged to the exterior by going through body (2) and this maintains the state of humidity and heat preservation while the user is using the mask.

In succession, air from the outside is inhaled into the body through the nose and mouth after going through a concentrated passage at the time of inhalation. At this time, inhalation of the air from the outside takes place through the concentrated passage that maintains state of heat and humidity preservation due to repetitive prior exhalation. Accordingly, cold and dry air that can exert a negative influence on a patient with a cold is transformed into more warm and humid air by inhalation. As a consequence, the present invention helps prevent worsening of symptoms for a patient with a cold and can also improve related illness.

Moreover, when a patient wearing eyeglasses applies the mask (1) during winter, creation of frost on the surface of eyeglasses due to breath steam is prevented since the warm exhalation air steam is not discharged in the upper direction forward the glasses due to the air-blocking material (5) that is placed at the inner surface of body (2), and since most of the discharged steam goes through the concentrated passageways. Accordingly, a user of eyeglasses can apply the mask (1) with utmost convenience.

Moreover, air-blocking material (5) that forms the concentrated passageway arranged between body (2) and the surface of the face is preferably comprised of soft, light and elastic material. Accordingly, elasticity is induced at the time of wearing the mask, which in turn induces elasticity in the area located between two ears and in the hanging string (3), attached onto the left and right side of body (2). As a consequence, pain in both ears, caused by the pressing down of hanging strings (3) may be prevented, increasing the comfort of the user.

The above specification provides explanation and figures pertaining to specific examples. It is noteworthy that anyone in the applicable industry with an ordinary expected level of pertinent knowledge will understand that the present invention may be reformed and changed in diverse forms within the boundaries of the spirit and scope of the hereinafter stated claims.

What is claimed is:

1. A health mask for covering the nose and mouth of a user, said mask comprising:
    a body sized to cover the nose and mouth of a user and including user attachment structure attached to opposite sides of the body;
    said body including a pair of air blocking members, each member extending both horizontally away from an area where a user's nose is to be placed during use and vertically downwardly towards an area where the user's mouth is to be placed during use thereby forming concentrated air passageways for inhalation and exhalation air during use.

2. A health mask as in claim 1 wherein said air blocking members comprise symmetrical inverted L-shaped structures.

3. A health mask as in claim 2 wherein lower ends of said air blocking members each terminate proximate an area where an edge of the user's mouth is to be placed during use.

4. A health mask as in claim 3 wherein said air blocking members are affixed to a supporting member by adhesion upon impact.

5. A health mask as in claim 2 wherein said air blocking members are affixed to a supporting member by adhesion upon impact.

6. A health mask as in claim 1 wherein lower ends of said air blocking members each terminate proximate an area where an edge of the user's mouth is to be placed during use.

7. A health mask as in claim 6 wherein said air blocking members are affixed to a supporting member by adhesion upon impact.

8. A health mask as in claim 1 wherein said air blocking members are affixed to a supporting member by adhesion upon impact.

* * * * *